United States Patent
Andelin et al.

(10) Patent No.: US 10,277,355 B2
(45) Date of Patent: Apr. 30, 2019

(54) BEAM PHASING METHOD AND APPARATUS FOR ADJUSTING A TIMING OF BEAM PROJECTIONS

(71) Applicant: FFE Limited, Hertfordshire (GB)

(72) Inventors: Jacob Andelin, Hertfordshire (GB); Marcus Perch, Hertfordshire (GB)

(73) Assignee: FFE LIMITED (GB)

(*) Notice: Subject to any disclaimer, the term of this patent is extended or adjusted under 35 U.S.C. 154(b) by 177 days.

(21) Appl. No.: 15/627,667

(22) Filed: Jun. 20, 2017

(65) Prior Publication Data
US 2017/0366292 A1    Dec. 21, 2017

(30) Foreign Application Priority Data

Jun. 21, 2016 (GB) .................... 1610856.5

(51) Int. Cl.
| | |
|---|---|
| *G01S 17/88* | (2006.01) |
| *H04J 14/08* | (2006.01) |
| *G01N 21/53* | (2006.01) |
| *G08B 29/18* | (2006.01) |
| *G06F 7/58* | (2006.01) |
| *G08B 17/103* | (2006.01) |
| *G01N 21/3504* | (2014.01) |

(52) U.S. Cl.
CPC ............ *H04J 14/08* (2013.01); *G01N 21/53* (2013.01); *G01S 17/88* (2013.01); *G06F 7/58* (2013.01); *G08B 17/103* (2013.01); *G08B 29/18* (2013.01); *G01N 21/3504* (2013.01); *G01N 2201/0699* (2013.01)

(58) Field of Classification Search
CPC ............ G01S 17/88; G06F 7/58; H04J 14/08
USPC .......................................................... 250/221
See application file for complete search history.

(56) References Cited

U.S. PATENT DOCUMENTS

| | | | |
|---|---|---|---|
| 2,886,811 A * | 5/1959 | Harrison, Jr. ............ | H01Q 3/44 342/121 |
| 3,924,252 A | 12/1975 | Duston | |

(Continued)

FOREIGN PATENT DOCUMENTS

| | | |
|---|---|---|
| EP | 0772852 B1 | 12/1998 |
| GB | 2000863 A | 1/1979 |

(Continued)

OTHER PUBLICATIONS

Great Britain Combined Search and Examination Report for Great Britain Application No. GB1610856.5, dated Dec. 16, 2016—4 Pages.

(Continued)

*Primary Examiner* — Que Tan Le
(74) *Attorney, Agent, or Firm* — RatnerPrestia

(57) ABSTRACT

A method for adjusting the timing of beam projections in a beam detector. The method includes projecting a beam for the purpose of detecting obscuration of the beam and, if a level of signal of the beam detected is less than a threshold for each of a number of consecutive projections or for each consecutive projection over a pre-determined time period, initiating a warning, signalling an alarm or otherwise reacting. The method further includes adjusting the timing of projecting the beam from a nominal transmit interval 'T' to be within a window time-period 'W' extending from an amount before to an amount after the nominal transmit interval 'T'.

19 Claims, 2 Drawing Sheets

(56) References Cited

U.S. PATENT DOCUMENTS 5,864,293 A 1/1999 Lewiner
2015/0160175 A1 6/2015 Knox et al.

FOREIGN PATENT DOCUMENTS

GB 2158627 A 11/1985
WO 2010032198 A1 3/2010

OTHER PUBLICATIONS

Siebel, et al., "Test of fire detection algorithms using artificially generated events", Fire Safety Journal, Elsevier, vol. 41, No. 4, pp. 258-265, Apr. 17, 2006.
European Search Report of Application No. EP 17 17 7062 dated Oct. 24, 2017.

* cited by examiner

BEAM PHASING METHOD AND APPARATUS FOR ADJUSTING A TIMING OF BEAM PROJECTIONS

CROSS-REFERENCE TO RELATED APPLICATION

This Patent Application claims priority from UK Patent Application No. GB1610856.5, filed Jun. 21, 2016, the disclosure of which is incorporated by reference herein in its entirety.

FIELD OF THE INVENTION

The present invention relates to randomly, pseudo-randomly or otherwise adjusting the phasing of beams. In particular, the invention relates to: a method for adjusting the phasing of beams in a beam detector; a beam detector apparatus; and an associated beam detector system.

BACKGROUND OF THE INVENTION

In summary, a reflective optical beam smoke detector system has a detector unit, which includes both a transmitter and a receiver, and a retro-reflector. The detector unit and the reflector are placed opposite each other at opposing ends of a volume to be protected and monitored. The transmitter projects a modulated beam, in this example a modulated Infrared (IR) beam, on to the retro-reflector which reflects the IR beam along the same axis back to the receiver. Smoke in the beam path will reduce the amount of light returning to the receiver. The receiver continuously monitors the amount of light received and, if it drops below a certain user-defined threshold, then an alarm is initiated. Typically, the beam is not continuously projected, but only once per second for a very short time ~10 milliseconds (ms).

Installing two such detectors in an opposite manner comes with both advantages and disadvantages. This configuration is advantageous if the volume which is to be protected is longer than the specified protection distance of a detector. In that situation, which is not uncommon, if the distance is anything larger, an installer will install a detector on each wall, and install reflectors back-to-back at an approximate midway point between them. The advantage of this is that all of the electrical wiring to power supplies and fire panels remains at the edges of the building, rather than having to run such wiring to midpoints in a volume to be protected. Unfortunately, although there are advantages to this configuration, it is also the cause of problems, as the beam from one detector will fall upon the opposite detector unit. This scenario is exemplified in FIG. 1.

FIG. 1 illustrates a prior art detector system, identified generally by reference 100, which includes a first detector unit 110 and a second detector unit 120. In this example, the detector units are operating with Infrared (IR) light. Detector unit 110 includes both a transmitter and a receiver within the unit 110 and, as for detector unit 120, it also includes a transmitter and receiver within the unit 120. Each of the units 110; 120 is located in an opposed manner (as shown in FIG. 1) and have a corresponding reflector 111; 121, respectively, located within a volume to be monitored at a location some distance from the units 110; 120 and towards which a beam is projected by the detector units 110; 120. The corresponding reflectors 111; 121 are neither provided exactly equidistant nor centrally between the two detectors units 110; 120, although this is not an unusual configuration. Each unit 110; 120 operates independently of the other, such that if obscuration of the beam occurs between detector unit 110 and corresponding reflector 111, and between detector 120 and corresponding reflector 121, a warning or alarm is independently signalled or activated. Of course, if obscuration occurs in both regions, then two alarms would be signalled or activated. There are, of course, advantages or reasons as to why it would be useful or necessary to locate detector units 110; 120 in an opposed manner, even though there is a chance, or even likelihood, that some of the beam projected from one might interfere with detection of the beam of the other unit.

Using the beam 122 from detector unit 120 as an example, and as shown in FIG. 1 in particular, normal detection can occur between the unit 120 and its reflector 121, as per normal operation of the beam detector. However, in relation to part 122' of the beam 122 which projects past the reflector 121 and illuminates the environs of the detector 110, as indicated by illuminated regions 101 and 102, and a corresponding shadow region 103 caused by the reflector 121 in the beam 122, if detector unit 120 is projecting its beam 122 at a same time as detector unit 110 is expecting to receive its own projected beam (not shown), there is a strong chance that detector unit 110 will receive more light than expected, some of which from beam part 122'.

As the detector units 110; 120 only transmit for 10$ms$ every second, this does not cause a continuous problem as the two units will often transmit at different times. However, owing to timing differences between the two detectors, they will eventually come into phase where they will transmit at the same time. Each detector will not only receive light from its own reflector but also light from the opposite transmitter. As the beams are modulated, depending upon how the peaks and troughs of the two beams coincide, this will cause an increase or decrease in the signal strength. The effect of this is that the effective signal strength received may go up or down at random, which leads to false alarms and the signalling of faults. Further, the phasing in and phasing out again of the beam transmissions can be somewhat random also, for example, the beams could be out of phase for hours, days or even weeks but once in phase they could be in this situation for minutes, hours or days, so it is hard to predict how long the beams will be in phase.

It is also known to place a baffle between a set of back-to-back reflectors, so as to increase the size of a shadow region caused by the light of opposed detector units, such that receiving units per se are within that shadow region. Such baffles are necessarily relatively large when compared to the reflectors and rather unsightly. The present invention is aimed at alleviating the above disadvantage(s) associated with beam detectors.

SUMMARY OF INVENTION

According to a first aspect, the present invention provides a method for adjusting the timing of beam projections in a beam detector, the method comprising projecting a beam for the purpose of detecting obscuration of the beam and, if a level of signal of the beam detected is less than a threshold for each of a number of consecutive projections or for each consecutive projection over a pre-determined time period, initiating a warning, signalling an alarm or otherwise reacting, wherein the method further comprising adjusting the timing of projecting the beam from a nominal transmit interval 'T' to be within a window time-period 'W' extending from an amount before to an amount after the nominal transmit interval 'T'.

Preferably, the nominal transmit interval 'T' is a regular interval.

Preferably, pseudo-randomly or randomly adjusting the timing.

Preferably, the amount before and the amount after are (approximately) equal time periods.

Preferably, 'W'≤'T'. Preferably 'W'='T'/2. Most preferably, 'W' is symmetrical about 'T'.

Preferably, if a length of time of projection of the beam is 'L', 'W'≥2'L' to 'W'>>2'L'. In which, '>>' is the well-known operator 'much greater than'.

As such, the projected beam may be projected at some time before the next nominal transmit interval, on the next nominal transmit interval or after the next nominal transmit interval.

Preferably, using a pseudo-random number sequence to adjust the timing of projection.

Most preferably, using an initial light intensity reading, start-up time, or A-to-D (analogue-to-digital) converter input to generate the pseudo-random number sequence.

Preferably, 'T' is about 0.1 to about 10 seconds, further preferably about 0.5 to about 5 seconds and, most preferably, about 1 second. Preferably, 'W' is about 0.05 to about 10 seconds, further preferably about 0.25 to about 5 seconds and, most preferably, about 0.5 seconds. Preferably, 'L' is about 1 millisecond to about 25 milliseconds, further preferably about 5 milliseconds to about 20 milliseconds and, most preferably, about 8 milliseconds to about 12 milliseconds or about 10 milliseconds. Most preferably, 'T' is one second, 'W' is 500 milliseconds and 'L' is 10 milliseconds.

Preferably, the beam detector is an optical beam smoke detector, preferably a reflective-type optical beam smoke detector.

Otherwise reacting comprises any form of audible and/or visual stimuli, and/or even the triggering of remedial fire apparatus, for example sprinklers or the like.

According to a second aspect, the present invention provides a beam detector apparatus, for adjusting the timing of beam projections in a beam detector, comprising:
   projecting apparatus for projecting a beam for the purpose of detecting obscuration of the beam and, if a level of signal of the beam detected is less than a threshold for each of a number of consecutive projections or for each consecutive projection over a pre-determined time period, initiating a warning, signalling an alarm or otherwise reacting; and
   adjusting apparatus for adjusting the timing of projecting the beam from a nominal transmit interval 'T' to be within a window time-period 'W' extending from an amount before to an amount after the nominal transmit interval 'T'.

Preferably, the beam detector apparatus is for providing pseudo-randomly or randomly phased beams.

Preferably, the means for adjusting comprises means for generating a random number sequence.

Preferably, the means for adjusting comprises means for taking an initial light intensity reading and generating the random number sequence.

Preferably, the means for projecting is a reflective-type optical beam smoke detector, comprising a transmitter and receiver in the same detector unit, and an associated reflector. Alternatively, the means for projecting is an end-to-end optical beam smoke detector, comprising separate transmitter and receiver units.

Preferably, the nominal transmit interval 'T' is a regular interval.

Preferably, the apparatus includes one or more features from the first aspect.

According to a third aspect, the present invention provides a beam detector system, for adjusting the timing of beam projections, the system comprising: a first transmitter and associated receiver; and a second transmitter and associated receiver, the first and second transmitters are arranged in opposing configuration such that, during normal operation, an amount of light from the transmitter of one pair may be incident on the receiver of the other pair and
in which each pair of transmitter and receiver, although opposing, operate independently of the other pair by each projecting beams for the purpose of detecting obscuration of the beams such that, if a level of signal of the beams detected is less than a threshold for each of a number of consecutive projections or for each consecutive projection over a pre-determined time period, then initiating a warning, signalling an alarm or otherwise reacting;
   wherein, in order to avoid fluctuations in signal strength in use from any such incident light, at least one transmitter comprises adjusting apparatus for adjusting the timing of projecting the beam from a nominal transmit interval 'T' to be within a window time-period 'W' extending from an amount before to an amount after the nominal transmit interval 'T'.

Preferably, each transmitter comprises means for adjusting the timing of projecting the beam within a window time-period 'W' extending from an amount before to an amount after the nominal transmit interval.

Preferably, the means for adjusting is for providing pseudo-randomly or randomly phased beams.

Preferably, the means for adjusting comprises means for generating a random number sequence.

Most preferably, the means for adjusting comprises means for taking an initial light intensity reading and generating the random number sequence.

Preferably, wherein the system comprises a multiplicity of pairs of transmitter and receiver, subject to the size of the volume to be monitored. For instance, 3 to 100 pairs of transmitter and receiver, more preferably 3 to 30 pairs, or most preferably 3 to 10 pairs.

Preferably, each of the first or second transmitter and associated receiver is a reflective-type optical beam smoke detector, comprising a transmitter and receiver in the same detector unit, and an associated reflector. Alternatively, each of the first or second transmitter and associated receiver is an end-to-end optical beam smoke detector, comprising separate transmitter and receiver units. Further alternatively, the invention may comprise a combination of one or more reflective-type optical beam smoke detectors and one or more end-to-end optical beam smoke detectors.

Preferably, the nominal transmit interval 'T' is a regular interval.

Preferably, the system comprises a computer or the like, or software for generating a random number sequence and utilising that random number sequence so as to alter the timing of beam projections.

Preferably, the apparatus includes one or more features from the first aspect.

Advantageously, the present invention adjusts the timing of the beam signal of a beam detector within a window of possible timings, so as to lower the chance of any opposed detector unit projecting a corresponding beam at the same time, whilst maintaining consistency. Consistency is important. By maintaining the nominal time interval, the overall response time for the detector is kept constant because the speed of response of the detector to smoke is, typically, defined in terms of a 'fire delay'—which is a number of consecutive alarm condition readings required before the detector signals an alarm. As such, for a default delay of 10 seconds, the detector must detect an alarm condition 10 times in a row (at one second intervals of the nominal time interval) before an alarm is signalled. Without linking the random or pseudo-random timing of the beam signals to a window of the nominal time interval, then ten readings in a row could take significantly less than or more than 10 seconds, which would make the timing of the triggering of the alarm somewhat random also, and consistency of the overall response time would be lost.

As a detector system will only signal an alarm after a number of consecutive positive detection readings, which can be any number from, say, 2 to 30, this, together with the randomness of timing of the signal, acts to minimise the effects of a single in-phase timing of beam projections in opposed detector units. As such, the probability of there being a number of consecutive in-phase beam projections from the two detector units which would trigger a false alarm reduces with each consecutive projection, which means that the probability of false alarms having this cause reduces as one increases the number of consecutive positive readings required for signalling an alarm.

BRIEF DESCRIPTION OF FIGURES

The invention will now be disclosed, by way of example only, with reference to the following drawings, in which.

DETAILED DESCRIPTION

Figure 1:
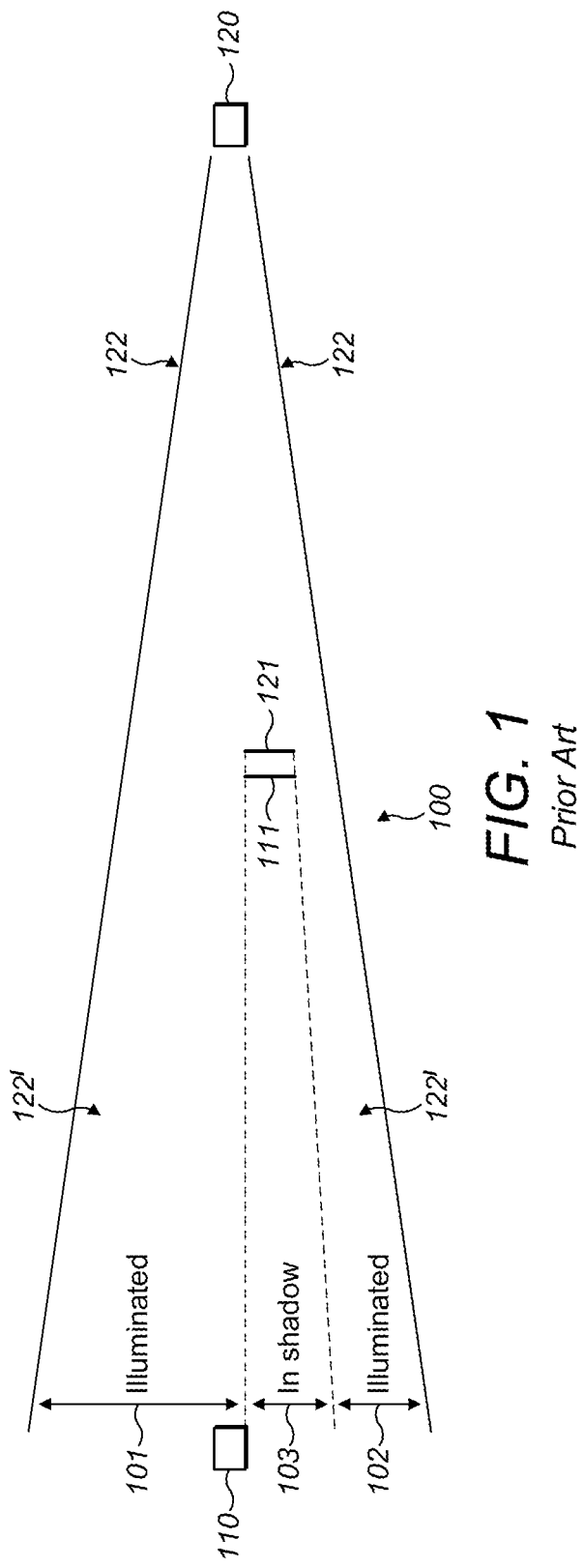
FIG. 1 is a schematic drawing of a prior art detector system.
Figure 2:
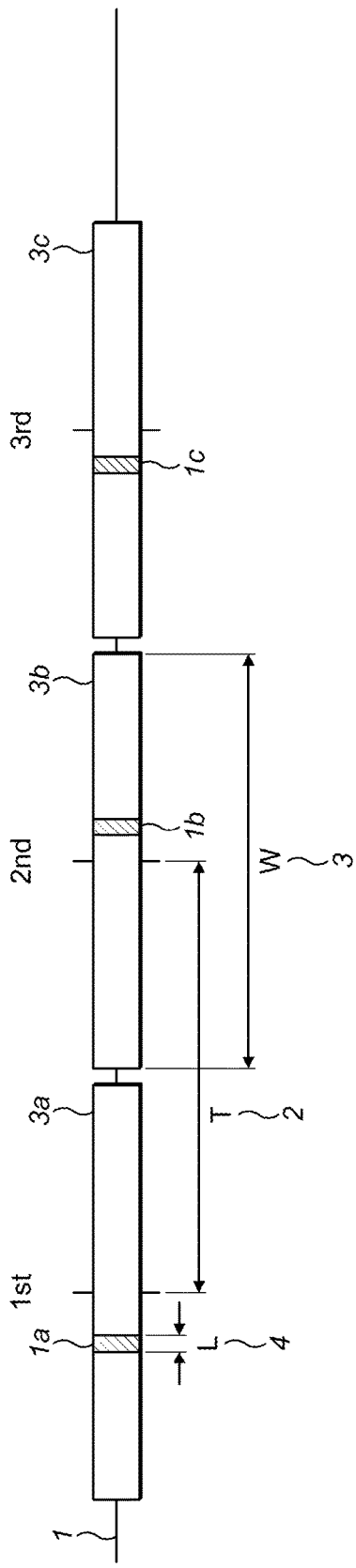
FIG. 2 is a schematic drawing of a series of pulsed transmission signals of a beam in a beam detector system according to the present invention.

With respect to FIG. 2, which shows a series of pulsed transmission signals 1 of a beam at $1^{st}$, $2^{nd}$ and $3^{rd}$ intervals, as is typical with beam detectors, the beams are not active all the time and FIG. 2 shows first through to third pulsed signals 1a, 1b, and 1c. FIG. 2 also shows: a repeating nominal transmit interval 'T', which is also indicated by reference 2 and which identifies the nominal transmit interval if the system was projecting beams at regular time intervals; a window time-period 'W', which is also indicated by reference 3 and which extends from an amount before to an amount after the nominal transmit interval 'T, being a period of possible times during which the pulsed beam signal can be projected; and a length of time 'L', also indicated by reference 4, being the length of time of transmission of the beam signal.

Unlike a system which projects a beam signal exactly in a regular manner at a regular time interval, the invention links randomness of the projection to the nominal time interval 'T' by creating respective window time-periods 'W' around respective nominal time intervals 'T', so as to provide randomness or pseudo-randomness of projection whilst maintaining consistency of response, as the time to trigger an alarm is unaffected by the randomness Owing to the window time-period 'W' during which the projection may occur, random or pseudo-random projection of the beam signal 1 can occur at any point during the window time-period 'W' such that it can occur before or after each respective nominal time interval 'T', or even at the nominal time interval 'T', but it would then be expected that a following projection would not occur on a following nominal time interval 'T'. As such, the time to trigger a response is a function of the nominal time interval 'T', not the actual (random) time intervals between projections, which provides consistency of response.

In FIG. 2, three windows are shown, 3a, 3b and 3c, which correspond to the pulsed signals 1a to 1c. In window 3a, signal 1a is projected before a first nominal time interval; in window 3b, signal 1b is projected after a second nominal time interval; and, in window 3c, signal 1c is projected before a third nominal time interval. These are just examples of possible timings of the beam signals 1a through to 1c which can occur in the windows 3a through to 3c.

The random/pseudo-random number sequence is provided by embedded software, which generates the sequence in a defined manner. The means for adjusting/adjusting apparatus for adjusting the timing of projecting the beam from a nominal transmit interval 'T' to be within a window time-period 'W' extending from an amount before to an amount after the nominal transmit interval 'T' is a computer controller or a microprocessor which, preferably, utilises the embedded software so as to generate the random/pseudo-random number sequence.

Figure 3:
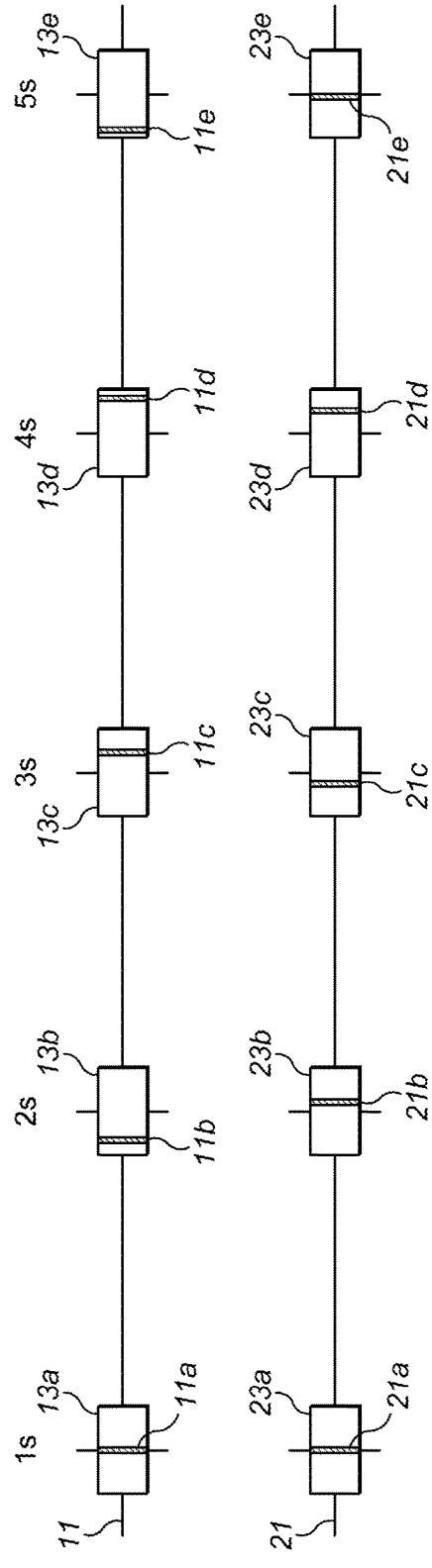
FIG. 3 is a schematic drawing of two series of pulsed transmission signals of beams from first and second opposed detector units in a beam detector system according to the present invention.

FIG. 3 shows series of signals 11; 21 respectively—shown side-by side—from a first detector unit and a second detector unit (not shown) but nominally referred to as detector units 10; 20 so as to avoid confusion. Each detector unit 10; 20 is independently operating on the principles as described in relation to FIG. 2.

In this worked example, each detector unit 10; 20 is operating upon a nominal transmit interval 'T' of one second, and the first five seconds of signals are shown in FIG. 3. The length of each signal 'L' is short, for example 10 milliseconds. The window time-periods of operation of the beams, indicated as references 13a through to 13e for detector unit 10, and 23a through to 23e for detector unit 20, are in phase and each first signal 11a; 21a is projected after a first nominal transmit interval of one second. The subsequent one second, nominal transmit intervals are identified by 2s, 3s, etc. After the first projections which occur together, timing of subsequent projections of the beams is randomly altered within the respective window time-periods 13b through to 13e and 23b through to 23e. By way of example, in window time-period 13b, the timing of projection of signal 11b is before a second nominal time interval, and yet the timing of signal 21b in window 23b is after. In window 13c, signal 11c is after a third nominal time interval and the timing of signal 21c in window 23c is before. In windows 13d and 23d, the timing of signals 11d; 21d are both after a fourth nominal time interval, but still at different times within the windows 13d and 23d. In window 13e, the timing of signal 11e is before a fifth nominal time interval and in window 23e, the timing of signal 21e is again (practically) on the nominal time interval.

Therefore, FIG. 3 seeks to provide a graphical example of signals 11; 21 from the respective detector units being projected at different times within their respective windows 13; 23. In this manner, this reduces the likelihood of the beam from one detector unit causing a false alarm by being detected by a separate detection unit.

What is claimed is:
1. A method for adjusting a timing of beam projections in a beam detector, the method comprising:

projecting a beam for a purpose of detecting obscuration of the beam, wherein, if a level of signal of the beam detected is less than a threshold for each of a number of consecutive projections or for each consecutive projection over a pre-determined time period, the method comprises the step of initiating a warning, signalling an alarm or otherwise reacting, and adjusting the timing of projecting the beam from a nominal transmit interval 'T' to be within a window time-period 'W' extending from an amount before to an amount after the nominal transmit interval 'T'.

2. The method as claimed in claim 1, further comprising pseudo-randomly or randomly adjusting the timing of the beam.

3. The method as claimed in claim 1, comprising one or more of:

'W'≤'T' or 'W'='T'/2, or 'W' is symmetrical about 'T'; and if a length of time of projection of the beam is 'L', then 'W'≥2'L' to 'W'>>2'L'.

4. The method as claimed in claim 1, further comprising using a pseudo-random number sequence to adjust the timing of projection.

5. The method as claimed in claim 4, further comprising using an initial light intensity reading, start-up time, or A-to-D converter input to generate the pseudo-random number sequence.

6. The method as claimed in claim 1, comprising one or more of:

'T' is about 0.1 to about 10 seconds;

'W' is about 0.05 to about 10 seconds; and

'L' is about 1 millisecond to about 25 milliseconds.

7. The method as claimed in claim 6, wherein 'T' is one second, 'W' is 500 milliseconds and 'L' is 10 milliseconds.

8. A beam detector apparatus, for adjusting a timing of beam projections in a beam detector, comprising:

a projecting apparatus for projecting a beam for a purpose of detecting obscuration of the beam and, if a level of signal of the beam detected is less than a threshold for each of a number of consecutive projections or for each consecutive projection over a pre-determined time period, initiating a warning, signalling an alarm or otherwise reacting; and an adjusting apparatus for adjusting the timing of projecting the beam from a nominal transmit interval 'T' to be within a window time-period 'W' extending from an amount before to an amount after the nominal transmit interval 'T'.

9. The beam detector apparatus as claimed in claim 8, wherein the projecting apparatus is:

a reflective-type optical beam smoke detector, comprising a transmitter and receiver in the same detector unit, and an associated reflector; or an end-to-end optical beam smoke detector, comprising separate transmitter and receiver units.

10. The beam detector apparatus as claimed in claim 8, wherein the adjusting apparatus is configured to generate a random number sequence.

11. The beam detector apparatus as claimed in claim 10, wherein the adjusting apparatus is configured to take an initial light intensity reading and generate the random number sequence.

12. A beam detector system, for adjusting a timing of beam projections, the system comprising:

a first transmitter and associated receiver constituting a first pair; and a second transmitter and associated receiver constituting a second pair, wherein the first and second transmitters are arranged in opposing configuration such that, during normal operation, an amount of light from the transmitter of one of the first pair and the second pair may be incident on the receiver of the other of the first pair and the second pair, and in which each pair of transmitter and receiver, although opposing, operate independently of the other pair by each projecting beams for the purpose of detecting obscuration of the beams such that, if a level of signal of the beams detected is less than a threshold for each of a number of consecutive projections or for each consecutive projection over a pre-determined time period, then initiating a warning, signalling an alarm or otherwise reacting;

wherein, in order to avoid fluctuations in signal strength in use from any such incident light, at least one of the transmitters comprises adjusting apparatus for adjusting the timing of projecting the beam from a nominal transmit interval 'T' to be within a window time-period 'W' extending from an amount before to an amount after the nominal transmit interval 'T'.

13. The beam detector system as claimed in claim 12, wherein each transmitter comprises an adjusting apparatus for adjusting the timing of projecting the beam from a nominal transmit interval 'T' to be within a window time-period 'W' extending from an amount before to an amount after the nominal transmit interval 'T'.

14. The beam detector system as claimed in claim 13, wherein the adjusting apparatus is configured to generate a random number sequence.

15. The beam detector system as claimed in claim 14, wherein the adjusting apparatus is configured to take an initial light intensity reading and generate the random number sequence.

16. The beam detector system as claimed in claim 12, wherein the system comprises at least three pairs of transmitter and receiver.

17. The beam detector system as claimed in claim 12, wherein each of the first or second transmitter and associated receiver is a reflective-type optical beam smoke detector, comprising a transmitter and receiver in the same detector unit, and an associated reflector.

18. The beam detector system as claimed in claim 12, wherein each of the first or second transmitter and associated receiver is an end-to-end optical beam smoke detector, comprising separate transmitter and receiver units.

19. The beam detector system as claimed in claim 12 comprising a computer controller or microprocessor having software for generating a random number sequence and utilizing the random number sequence so as to alter the timing of beam projections.

* * * * *